United States Patent [19]
Lalin et al.

[11] Patent Number: 4,896,548
[45] Date of Patent: Jan. 30, 1990

[54] FLUID SAMPLER WITH MINIATURE SINGLE-ACTING PUMP ASSEMBLY

[75] Inventors: Hill S. Lalin, Wayne; William T. Fleming, Glen Gardner, both of N.J.

[73] Assignee: Gilian Instrument Corp., Wayne, N.J.

[21] Appl. No.: 290,580

[22] Filed: Dec. 27, 1988

[51] Int. Cl.⁴ ............................................. G01N 1/14
[52] U.S. Cl. ............................... 73/864.34; 73/863.03
[58] Field of Search ........... 73/863.02, 863.03, 863.21, 73/863.23, 864.34, 864.35; 417/413

[56] References Cited

U.S. PATENT DOCUMENTS

| | | | |
|---|---|---|---|
| 4,432,248 | 2/1984 | Lalin | 73/863.03 |
| 4,532,814 | 8/1985 | Lalin | 73/863.03 |
| 4,576,054 | 3/1986 | Lalin | 73/863.03 |
| 4,743,169 | 5/1988 | Funakawa et al. | 417/413 |

Primary Examiner—John Chapman
Assistant Examiner—Michele Simons
Attorney, Agent, or Firm—E. Lieberstein

[57] ABSTRACT

The fluid sampler of the present invention comprises a single-acting pump assembly having a housing, an inlet port and an outlet port, a valve unit including a single inlet valve and a single outlet valve, a control diaphragm mounted in the housing to form a pumping chamber in communication with said inlet valve and said outlet valve, a reciprocative piston for reciprocating said control diaphragm, a motor for driving said piston with said piston being located in a substantially enclosed cavity separated from said pumping chamber by said control diaphragm and a damping assembly integrated in said pump housing for providing a highly damped fluid flow through said pump.

10 Claims, 7 Drawing Sheets

FLUID SAMPLER WITH MINIATURE SINGLE-ACTING PUMP ASSEMBLY

FIELD OF INVENTION

This invention relates to a fluid sampler containing a highly efficient miniature single-acting pump assembly for providing fluid flow through a load at preselected rates over a wide range of flow from as low as 2 cc per minute to as high as 4 liters per minute.

BACKGROUND OF THE INVENTION

Fluid samplers are regularly used to sample gases, particularly air, to determine the degree of exposure to hazardous chemicals. A typical sampling method involves collecting a sample of test gas, such as air, by drawing a known volume of the test gas through a collecting device. The collecting device may include a solid adsorbent (sorbent tube) capable of trapping and removing chemicals from the air or may include a filter for selectively collecting particulates, or a combination of both. This method is also applicable to wet test sampling referred to in the art as "impinger sampling." The test sample is then analyzed to determine the concentration level of the collected sample of chemicals or particulate matter. The method of analysis may involve gas chromatography or atomic adsorption, etc. For the analysis to be accurate, it is necessary to control the rate of fluid flow through the collecting device and it is preferable to use a calibrated flow rate.

All known pump sampling systems which control flow by adjustment of pump motor speed produce a pulsed air flow with relatively high pulse undulations at low flow levels. With a highly pulsed flow, it is difficult to set the flow rate. In fact, at very low flow rates, most common flow meters cannot be used to accurately determine or calibrate the flow because of their sensitivity, in part, to pulse magnitude as well as to actual net flow. High pulse undulations also tend to generate undesirable audible noise levels.

To minimize the amplitude of the pulse undulations at low flow rates and to reduce the noise level, a double-acting pump was typically used in conjunction with at least one damping assembly on the input suction side of the pump. A typical double-acting pump for contolling fluid flow in a fluid sampler over a wide range of flow rates is described in U.S. Pat. No. 4,432,248, assigned to the common assignee, Gilian Instrument Corporation, the disclosure of which is incorporated herein by reference. The fluid sampler incorporates two damping assemblies mounted in a common body with the double-acting pump. The damping assemblies communicate with the pump through an air port which connects the damper volumes to the pump intake. The double-acting pump and an electronically controlled pump motor speed control provides the fluid sampler described in the aforementioned patent with a regulated and smooth flow response over an operating pump flow range between 500 milliliters and 4 liters. Below 500 milliliters, the flow is unregulated, although still relatively smooth and noiseless.

For applications where it is important that the fluid sampler be very small in size as well as light in weight, a high efficiency, single-acting pump is preferable to the double-acting pump. A single-acting pump contains only one valve plate with one inlet valve and one exhaust valve. Accordingly, a fluid sampler with a single-acting pump draws fluid through a load on the intake stroke of the pump when the exhaust valve is closed and the intake valve is open. Conversely, fluid is discharged only during the exhaust stroke of the pump with the exhaust valve open and the intake valve closed. Thus with only one inlet valve and one exhaust valve, the single-acting pump at low flow rates will inherently cause large pulse swings. Although the large undulations in flow may be reduced by means of a damper located at the input to the pump, the flow response will not be as smooth in flow characteristic to that of the double-acting pump.

SUMMARY OF THE INVENTION

It has been discovered in accordance with the present invention that the smooth flow characteristic of the double-acting pump can be achieved using a single-acting pump with a "close-coupled" damping assembly. The "close-coupled" damping assembly is integrated into the single-acting pump assembly in such a way that the damper volume pneumatically and synchronously interacts with the pump diaphragm to produce a supplemental damper response on both the suction and discharge stroke which minimizes undulations in flow. This produces a very smooth flow characteristic equivalent to a double-acting pump at flow rates below 1,000 cc per minute.

The fluid sampler of the present invention comprises a single-acting pump assembly having a housing in the form of a block with an inlet port and an outlet port, a valve unit including a single inlet valve and a single outlet valve, a control diaphragm mounted in the housing to form a pumping chamber in communication with said inlet valve and said outlet valve, a piston for reciprocating said control diaphragm, a motor for driving said piston with said piston being located in a substantially enclosed cavity, separated from said pumping chamber by said control diaphragm and damping means integrated in said pump housing for providing a highly damped fluid flow through said pump assembly, said damping means comprising a damping chamber having a diaphragm in common with said damping chamber and said substantially enclosed cavity and a coil spring.

The fluid sampler of the present invention has a single-acting pump assembly with a close-coupled damping assembly integrated therein for sampling air flow through a load over a very wide flow range of between 2 cc per minute and 4 liters per minute. The fluid sampler is also adapted to receive any one of a plurality of "plug-in" modules for operating the fluid sampler at low flow conditions below about 500 cc per minutes, either in a constant flow mode of operation, a constant pressure mode of operation or in a bypass mode of operation.

BRIEF DESCRIPTION OF THE DRAWINGS

Other advantages of the present invention will become apparent from the following detailed description of the invention when read in conjunction with the following drawings of which.

DETAILED DESCRIPTION OF THE INVENTION

Figure 1:
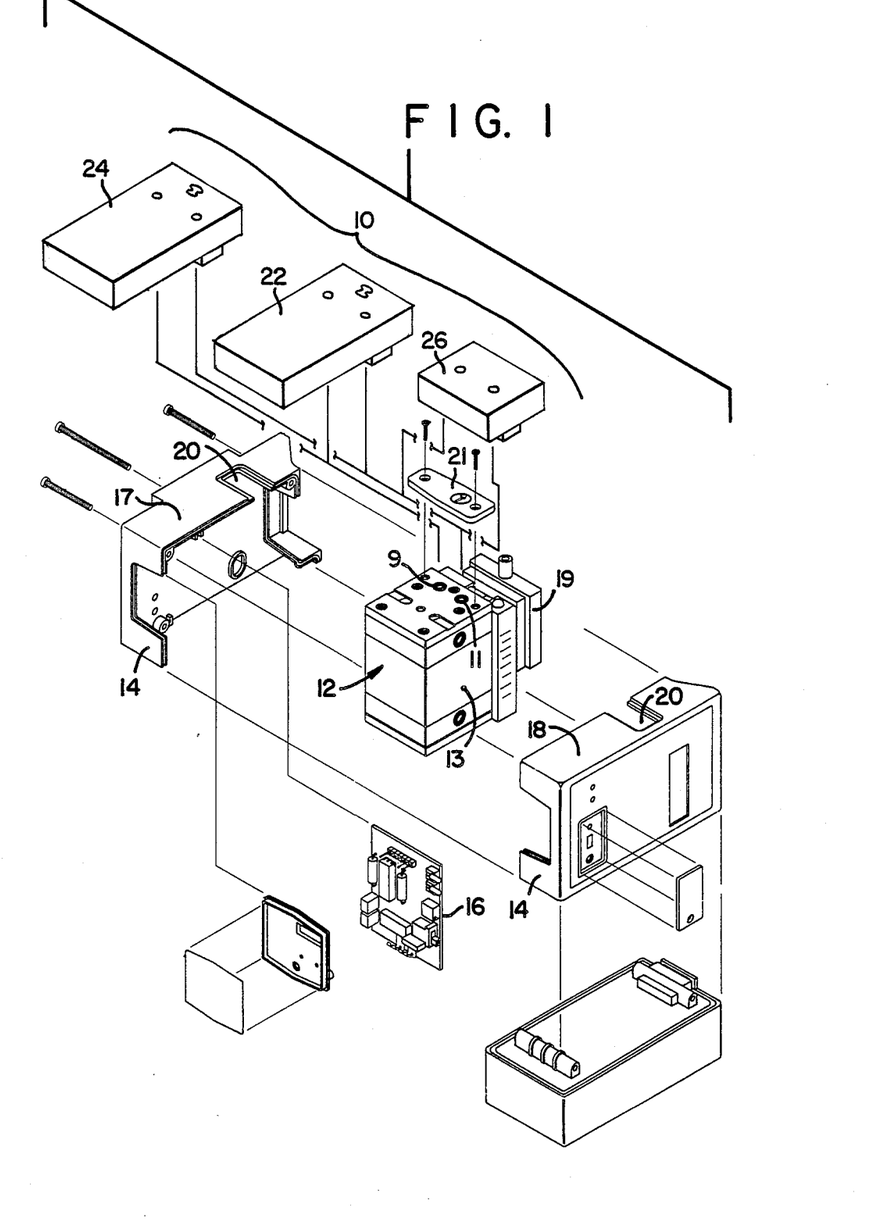
FIG. 1 is an exploded view in isometric showing the fluid sampler of the present invention and the alternative "plug-in" modules which may be separately inserted into the fluid sampler for low flow operation.
Figure 8:
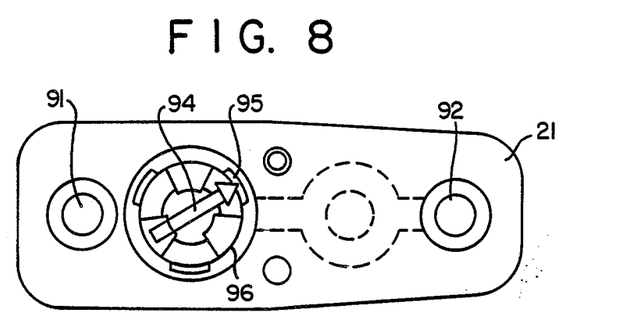
FIG. 8 is a top view of the vent bleed module assembly (20)
Figure 9:
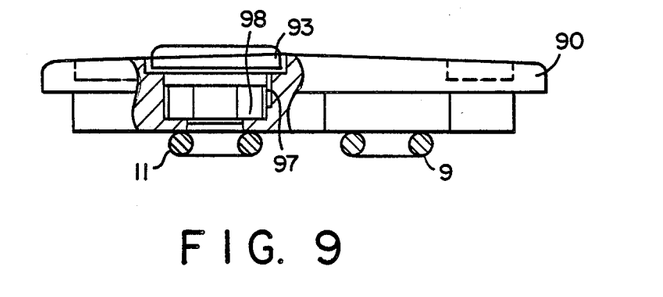
FIG. 9 is a view in side elevation of the vent bleed module assembly of FIG. 8.

The fluid sampler (10) of the present invention, as shown in FIG. 1 of the drawings, broadly comprises a single-acting vacuum pump assembly (12) mounted in a self-contained housing (13) in the form of a block, a battery pack (15) in which a plurality of DC batteries (not shown) are stored, an electronic motor control circuit (16), and a pneumatic assembly (19). The fluid sampler (10) is assembled into a common case (14) with the pump assembly (12) and motor control circuit (16) mounted over the battery pack (15). The common case (14) has a front panel (17) and a rear panel (18) which interfit, leaving an open slot (20) above the ports formed by "O" rings (9) and (11) of the vacuum pump assembly (12). The pneumatic assembly (19) includes a conventional flowmeter, such as a Rotometer (not shown) and a pump filter. The open slot (20) in the encasement (14) is closed by attachment of a plug (21) or by attachment of one of the three fluid flow control modules (22), (24) or (26), respectively. The plug (21) operates as a two-position switch to permit the user to vent the pump assembly (12) in the fluid sampler (10) to the atmosphere through the open slot (20) or to vent the pump assembly (12) interiorly of the housing (14). The plug (21) will be described more fully in connection with FIGS. 8 and 9.

Under low flow operation of from about 2 cc to 500 cc per minute, the plug (21) is removed and one of the three fluid flow control modules (22), (24) and (26) is coupled to the fluid sampler (10) through the slot (20) to regulate fluid flow. The choice between flow control modules (22), (24) or (26) is based upon whether the operation requires constant flow at a preselected low flow rate or constant pressure or for use at low flow where constant flow and constant pressure are not critical. The operation of the fluid sampler (10) at low flow will be described in connection with the schematic drawings of FIGS. 5-7 based upon the choice of attachment of one of the flow controls modules (22), (24) or (26), respectively. The fluid sampler (10) is operated in a conventional manner for drawing air through a load (not shown), so as to permit the quality of the air to be tested for impurity content. The single-acting vacuum pump assembly (12) permits the fluid sampler (10) to operate over a wide operating flow range of from 2 cc to 4 liters per minute.

Figure 2A:
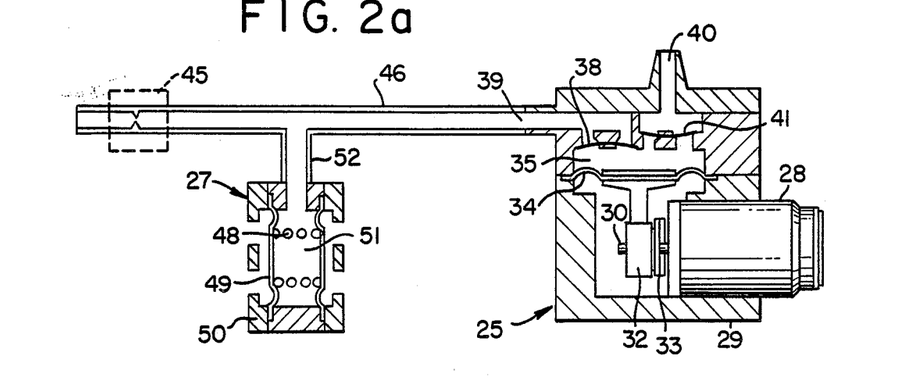
FIG. 2A is a schematic drawing of a typical fluid sampling system using a conventional single-acting pump assembly and an accumulator-type damping assembly.

In order to understand the principle of operation of the integrated single-acting pump and close-coupled damper of the present invention, a conventional single-acting pump assembly (25) will be briefly described in combination with a conventional accumulator-type damper (27). The arrangement for a convention pump assembly (25) and damper (27) is schematically shown in FIG. 2A. The conventional single-acting pump assembly (25) includes a DC motor (28) which is mounted in the pump assembly housing (29) with its shaft (30) coupled to a reciprocating piston (32) through an eccentric (33). The piston (32) is coupled to a pump diaphragm (34). The pump diaphragm defines one wall of a pumping chamber (35). The pumping chamber (35) communicates with the inlet port (37) of the pump assembly (25) through an inlet valve (38) which is open when the inlet valve (38) is in the open position, and communicates with the outlet port (40) through the outlet valve (41) which is open when the outlet valve (41) is in the open position. The inlet port (37) to the pump assembly (25) is connected to a load (45) through a conduit (46) for drawing air from the atmosphere through the load (45). The damper assembly (27) is connected in common with the load (45) to the pump assembly (25) through the input port (37). The damper assembly (27) basically includes a coil spring (48) separating two flexible diaphragms (49) and (50), respectively. The diaphragms (49) and (50) form an enclosed damper volume (51), within which the spring (48) is mounted. In this arrangement, the damper volume (51) is pneumatically connected through a conduit (52) to the inlet port (37) representing the suction side of the vacuum pump assembly (25). The DC motor (28) drives the reciprocating piston (32) from a source of DC power such as a battery supply (not shown).

Figure 2B:
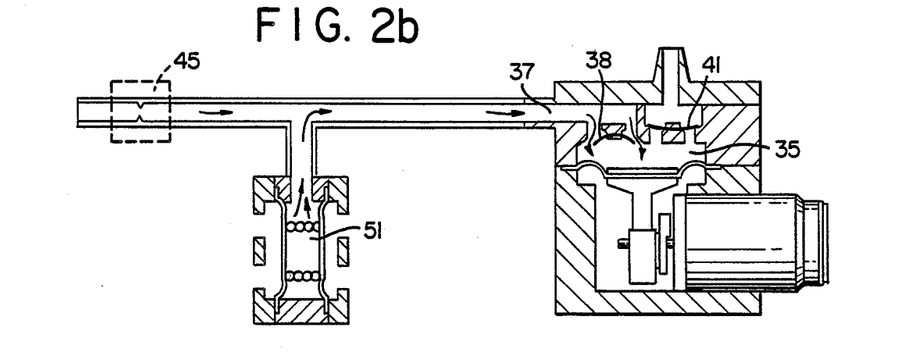
FIG. 2B shows the operation of the conventional pump and damping assembly of FIG. 2A during the intake stroke of the pump with the intake valve open.
Figure 2C:
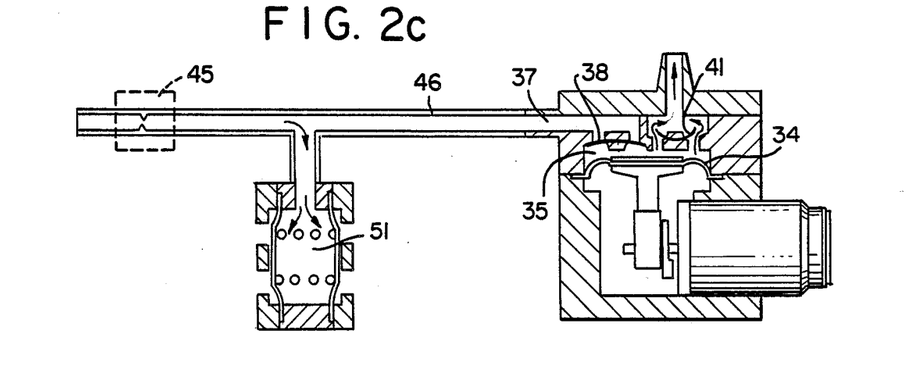
FIG. 2C shows the operation of the conventional pump and damping assembly of FIG. 2A during the discharge stroke of the pump with the exhaust valve open.

A single-acting pump cycle consists of an intake stroke and a discharge stroke. During the intake stroke, as shown in FIG. 2B, the pump diaphragm (34) is moved downward so as to expand the volume in the pumping chamber (35). This expansion is accompanied by a decrease in the pressure within the pumping chamber (35) which opens the inlet valve (38) and holds the outlet valve (41) closed. Air is drawn through the load (45) into the inlet port (37). The reduced pressure also draws air from the damper volume (51), as indicated by the arrows. During the discharge stroke, as shown in FIG. 2C, the pump diaphrapm (34) is moved upward, compressing the volume in the pumping chamber (35). The compression of the pumping chamber (35) closes the inlet valve (38) and opens the outlet valve (41). The pressure in the conduit (46) rises, which causes the damper volume (51) to expand. Air flows through the load into the damper volume (51), though there is little or no flow into the pump inlet port (37).

Figure 2D:
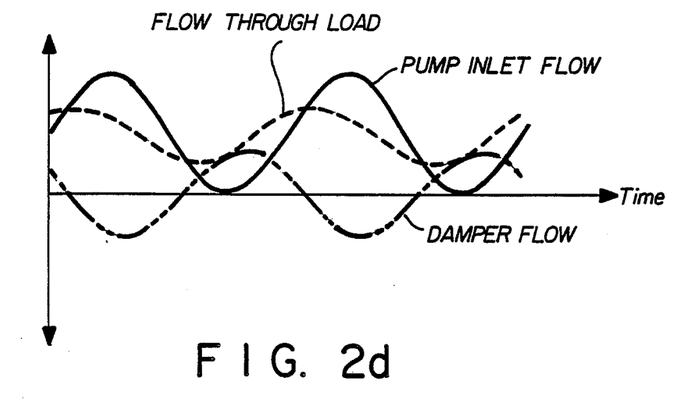
FIG. 2D shows a superimposed graph of the flow through the pump inlet; the flow through the damper and the flow through the load of FIG. 2A with each shown relative to the same time axis.

During the intake stroke, air is drawn from the damper (27) into the conduit (52) to supplement the air being drawn into the pump. During the exhaust stroke, air is drawn into the damper assembly (27) while air is being discharged from the pump. Flow through the pump, the damper assembly and the load is shown in FIG. 2D, superimposed upon one another. The flow through the damper is negative during most of the intake stroke and positive during most of the exhaust stroke. Since the flow through the load is the summation of flow through the pump and damper, the effect of the damper is to minimize pulse swings through the load.

Figures 3A, 3B:
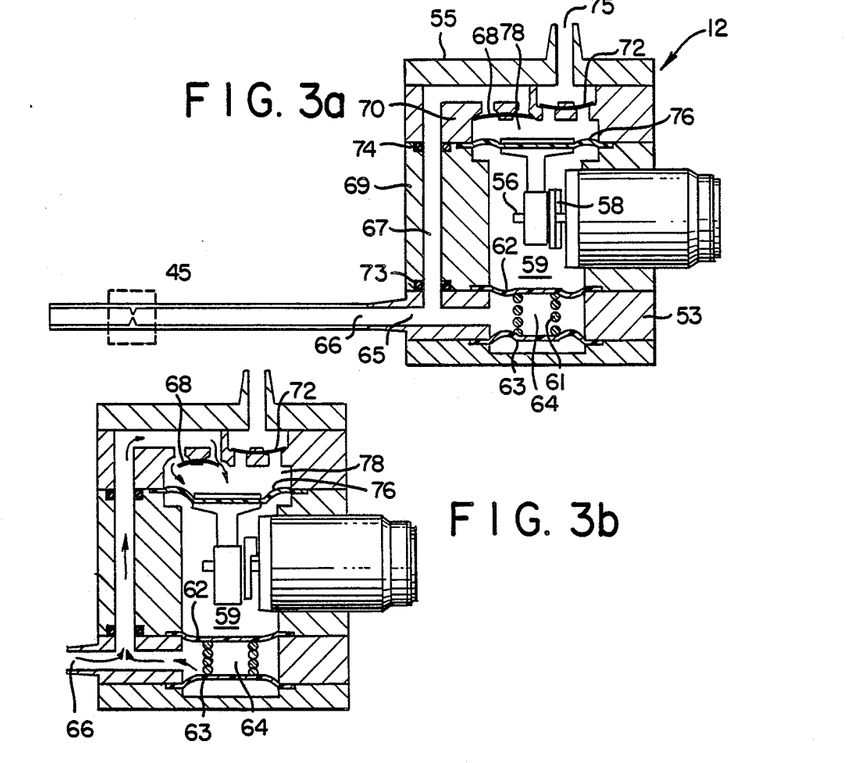
FIG. 3A is a schematic drawing of a fluid sampling system incorporating a single-acting pump assembly and a close-coupled damper in accordance with the present invention.
FIG. 3B shows the operation of the pump assembly of FIG. 3A during the intake stroke of the pump with the intake valve open.
Figure 3C:
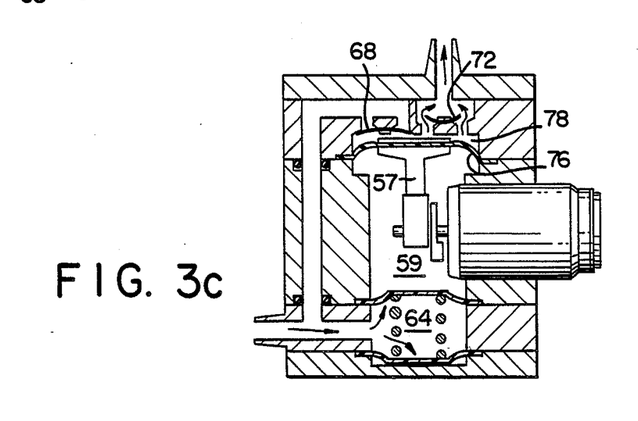
FIG. 3C shows the operation of the pump assembly of FIG. 3A during the discharge stroke of the pump with the exhaust valve open.
Figure 4:
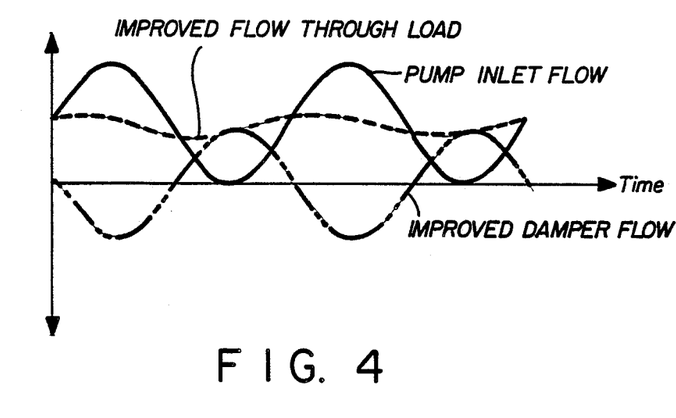
FIG. 4 shows a superimposed graph of the flow at the inlet to the pump assembly of FIG. 3; and flow through the integrated damper and the flow through the load all relative to time.

The improved close-coupled single-acting pump design of the present invention is illustrated in FIGS. 3A–3C, in conjunction with FIG. 4.

The single-acting pump assembly (12) of the present invention is schematically shown in FIG. 3(A). The pump assembly (12) has an integrated damper assembly (53) incorporated in a common housing (69) which supports a DC motor (M). The DC motor (M) is powered by the battery pack (15), with its speed controllably adjusted by the motor control circuit (16). A preferred electronic motor control circuit (16) is schematically shown and described in detail in U.S. Pat. No. 4,432,248, the description of which is herein incorporated by reference. Alternatively, any conventional electronic motor control circuit may be used to adjustably vary motor speed to control air flow, particularly for flow above 500 cc per minute.

The shaft (56) of the DC motor (M) is coupled to a reciprocating piston (57) through an eccentric (58). The DC motor (M) extends into a cavity (59) which forms a substantially enclosed volume in the pump assembly (12). The damper (53) is structurally equivalent to the damper assembly (27) of FIG. 2A and includes a coil spring (61) separating two flexible diaphragms (62) and (63), respectively, for defining a damper volume (64). One of the diaphragms (62) forms a common divider separating the substantially enclosed volume (59) from the damper volume (64), thereby forming the close coupling between the damper assembly (53) and the pump (12). The pump assembly (12) is miniature in size, having a block-like shape with a passageway (65) leading from the inlet port (66) to the damper volume (64) and another passageway (67) extending from the passageway (65) to the inlet valve (68). The passageway (67) extends through the housing (69) in which the DC motor (M) is mounted and through the valve plate (70). The valve plate (70) includes the inlet valve (68) and an exhaust valve (72). Two "O" rings (73) and (74) seal the passageway (67) at the interface between the member (69), the valve plate (70), and the damper assembly (13). An exhaust port (75) communicates with the exhaust valve (72).

The piston (57) is connected to a control diaphragm (76) supported between the valve plate (70) and the housing (69). The control diaphragm (76) forms a pumping chamber (78) for opening and closing the inlet valve (68) and exhaust valve (72).

The intake stroke begins by downward movement of the piston (57) and the control diaphragm (76). The pumping chamber (78) is expanded, opening the inlet valve (68) and closing the exhaust valve (72). As shown in FIG. 3B, the downward motion of the control diaphragm (76) communicates through the enclosed volume of cavity (59) with the common diaphragm (62) forcing the common diaphragm (62) to move downward in synchronism. This drives air out from the damper volume (64) as indicated by the arrows to supplement air drawn in from the inlet port (66) upon opening the inlet valve (68).

The exhaust stroke begins upon opening the exhaust valve (72) in response to the upward movement of the piston (57) and the control diaphragm (76). The pumping chamber (78) is compressed, opening the exhaust valve (72) and closing the inlet valve (68). As shown in FIG. 3C, the upward motion of the control diaphragm (76) communicates through the enclosed volume of cavity (59) expanding the damper volume (64) in synchronism with the movement of the control diaphragm (76). This draws air into the damper volume (64) from the load, as indicated by the arrows.

FIG. 4 shows the effect of the close-coupled damper on the flow response through the load. Flow through the pump (12), the integrated damper (53) and the load (45) is shown superimposed upon one another in FIG. 4. The flow through the load (45) is the summation of flow through the pump (12) and integrated damper (53) due to the pumping action. Since the damper (53) is synchronized in an out-of-phase relationship with the pumping action, the summation is a smooth flow with minimal undulation.

Figure 5:
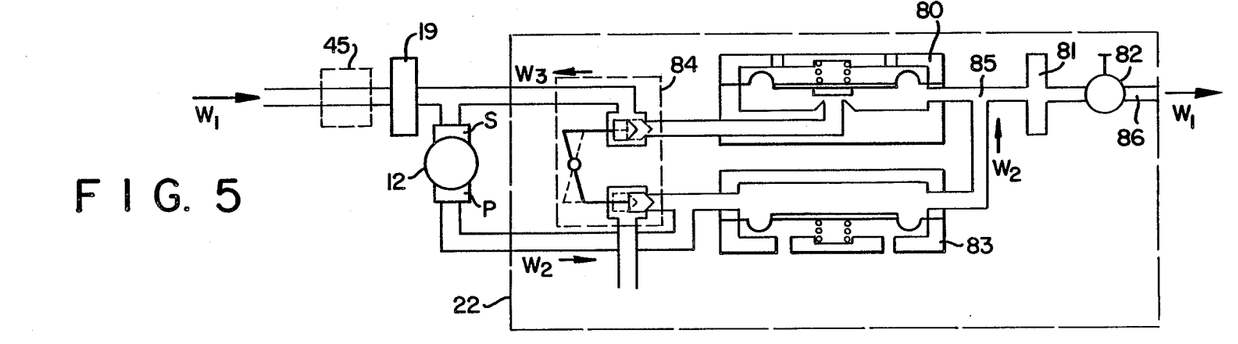
FIG. 5 is a system schematic diagram of the fluid sampler of FIG. 1 with the constant flow module attached.

The opeation of the fluid sampler (10) at low flow in a range of between 2 cc and 500 cc per minute is preferably carried out with one of the low flow control modules (22), (24) or (26) attached to the fluid sampler (10) through the slot (20). The fluid sampler (10) operates with a selected module (22), (24) or (26), as hereinafter explained in connection with the corresponding schematic flow diagram of FIGS. 5, 6 or 7, respectively. FIG. 5 is a system schematic diagram of the fluid sampler (10) with the constant flow module (22) attached to the pump (12). The module (22) includes a constant flow bypass regulator (80), a control valve filter (81), an adjustable control valve (82), a damper regulator (83) and a manually adjustable poppet shut-off valve (84).

The pump (12) of FIG. 5, and as earlier described in connection with FIGS. 3A–3C, includes the integrated damper assembly (53) and is driven by motor (M) with power supplied from the battery pack (15). The motor (M) operates under the control of a conventional motor control circuit (16), which regulates the voltage applied to the motor to maintain a preselected motor speed correlated to the pump load line curve, as taught in U.S. Pat. Nos. 4,432,238 and 4,747,315. The pump (12) causes air to be drawn from the atmosphere through the load (45) and through a pneumatic assembly (19) representing, for example, a conventional flowmeter and filter. Air is then drawn through the pump (12) and supplied under pressure to the bypass regulator (80), filter (81) and control valve (82), discharging to the atmosphere. The damper regulator (83) is an optional conventional damper for further reducing undulations in flow.

The poppet shut-off valve (84) in module (22) is a two-position switch which in the first position, as shown in FIG. 5, couples the bypass regulator (80) across the pump (12) between the suction side (S) and the discharge end (P), and in the second position, as indicated with dotted lines, operationally disconnects the module (22) from the fluid sampler (10), although the module (22) remains physically in the unit.

The module (22) with the poppet valve (84) in the open first position, as shown in FIG. 5, provides a bypass flow ($W_3$) which flows through the bypass regulator (80) to supplement the flow ($W_2$) through the pump (12) so that the flow ($W_1$) through the load (45) is constant. The flow ($W_3$) is regulated by the bypass regulator (80) to maintain a constant pressure at its discharge end (85) representing the input side of the control valve (82). The control valve filter (81) has essentially no pressure drop across it. The discharge end (86) of the control valve (82) is discharged to the atmosphere. Accordingly, by maintaining a constant pressure on the input side (85), a constant pressure differential across the control valve (82) is established, causing the flow ($W_1$) through the load to be constant.

The bypass regulator (80) operates to maintain the pressure constant at the discharge end (85) in accordance with the principles of operation taught in U.S. Pat. Nos. 4,532,814 and 4,576,054, the description of which is herein incorporated by reference. The actual low flow setting ($W_1$) is established by adjustment of the manually operated control valve (82).

Figure 6:
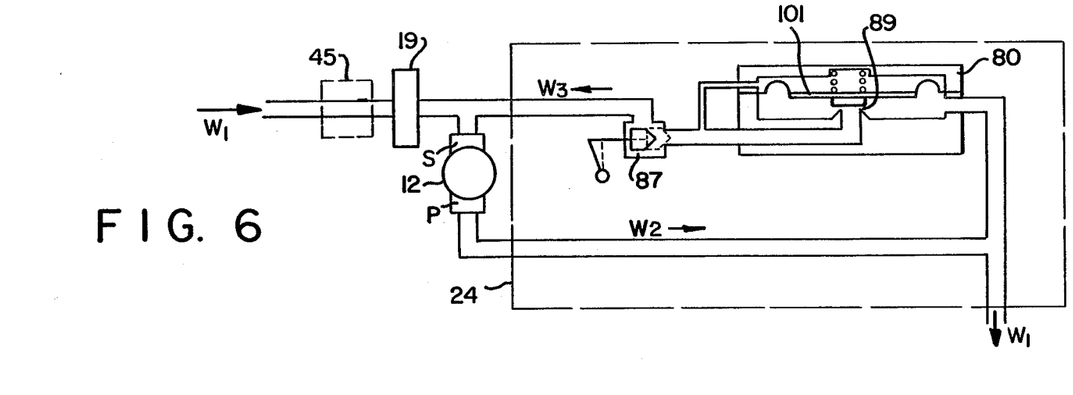
FIG. 6 is a system schematic diagram of the fluid sampler of FIG. 1 with the constant pressure module attached.

FIG. 6 is a system schematic diagram of the fluid sampler (10) with the constant pressure module (24) attached to the pump (12). In the constant pressure mode of operation, the bypass regulator (80) is coupled across the pump (12) to provide a bypass flow ($W_2$) around the pump (12) so that the discharge flow rate ($W_1$) is substantially equal to the flow ($W_1$) through the load (45). The regulator (80) maintains the pressure on the suction side (S) of the pump (12) constant by regulating the valve opening (89) in response to the pressure differential across the diaphragm (101). The regulator (80) operates as a suction pressure regulator to maintain a constant pressure on the suction side of the pump as disclosed in U.S. Pat. Nos. 4,432,248 and 4,576,054, the description of which is herein incorporated by reference. Since the pump is operationally in series with the load (45), the pressure across the load (45) is equal to the pressure at the inlet of the pump (12). The load (45) is intended, in this case, to represent a common manifold containing a multiple number of sorbent tubes, each of which is ported in series with an individual variable restrictor. By maintaining a constant pressure across the load (45), the flow rate through each sorbent tube may be individually determined by the setting of the individual restrictors.

The bypass regulator (80) in the flow arrangement of FIG. 6 operates to maintain a constant pressure in accordance with the more detailed explanation of U.S. Pat. No. 4,576,054, the description of which is herein incorporated by reference.

The constant pressure module (24) also includes a poppet valve (87) for disconnecting the regulator (80) from the operation of the system when switched from the position as shown in FIG. 6 to the position indicated with dotted lines.

Figure 7:
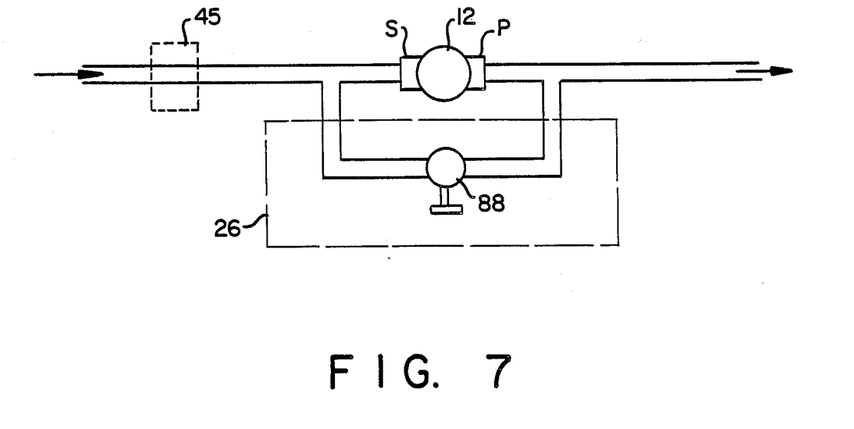
FIG. 7 is a system schematic diagram of the fluid sampler of FIG. 1, with the bypass module attached.

FIG. 7 is a system schematic diagram of the fluid sampler (10) with the bypass module (26) attached to the pump (12). The bypass module (26) consists solely of a manually adjustable bypass valve (88) which, as shown in FIG. 7, is connected across the discharge end (P) and suction side (S) of the pump (12). By manual adjustment of the bypass valve (88), the flow through the load (45) can be controllably varied to the desired flow setting. However, flow regulation is minimal. Nevertheless, for applications where flow regulation is not essential, it is the least expensive control.

During normal high flow operation, the plug (21) is used to close the slot (20). Plug (21) is a manually adjustable vent bleed assembly which permits venting to the atmosphere or internal venting within the casing of the fluid sampler (10). The plug (21) is shown in detail in FIGS. 8 and 9, consisting of a frame (90) conforming in shape and size to the slot (20). The frame (90) is attached to the pump (12) through screw holes (91) and (92). The plug (21) has a valve head (93) with a shallow slot (94) adapted to receive the end of a screwdriver for manually adjusting the valve head (93) so that the slot (94) is either aligned in the direction of the open position indicator (95), or in the direction of the closed position indicator (96). When the plug (21) is aligned in the direction of the open position indicator (95), air may freely travel through the passage (98) around the valve head (93) and through the slotted opening (97) to the atmosphere. When the plug (21) is aligned in the closed position, the valve head (93) closes off the slotted opening (97).

What is claimed is:

1. A fluid sampler for sampling air flow through a load comprising a single-acting pump assembly having a housing, an inlet port and an outlet port, a valve unit including a single inlet valve and a single outlet valve, a control diaphragm mounted in said housing to form a pumping chamber in communication with said inlet valve and said outlet valve, a piston for reciprocating said control diaphragm, a motor for driving said piston with said piston being located in a substantially enclosed cavity separated from said pumping chamber by said control diaphragm and damping means integrated in said pump housing for providing a highly damped fluid flow through said pump, said damping means comprising a first and second flexible diaphragm and a coil spring disposed between said diaphragms for forming a damping chamber with said first diaphragm disposed in common between said damping chamber and said substantially enclosed cavity.

2. A fluid sampler, as defined in claim 1, wherein said damping chamber is connected in common with the inlet port to the pump assembly and to said inlet valve.

3. A fluid sampler, as defined in claim 2, further comprising a pneumatic assembly and a battery pack enclosed in a common case having an open slot and a plurality of plug-in modules adapted to fit into said open slot.

4. A fluid sampler, as defined in claim 3, wherein a first one of said plug-in modules comprises a bypass regulator, a control valve, and means for coupling said bypass regulator to said pump assembly such that said bypass regulator maintains the pressure on one side of said control valve constant with the opposite side connected to the atmosphere for low flow control.

5. A fluid sampler, as defined in claim 4, wherein said pump housing has a discharge side and a suction side, and wherein said coupling means comprises a manually adjustable poppet valve having a first position for interposing the bypass regulator across the pump assembly such that the discharge side of the pump housing is in common between one end of the bypass regulator, and the control valve with the suction side of the pump housing connected to the opposite end of the bypass regulator.

6. A fluid sampler, as defined in claim 5, further comprising a damper regulator connected between the discharge side of the pump housing and the common connection between the bypass regulator and the control valve.

7. A fluid sampler, as defined in claim 3, wherein a second one of said plug-in modules comprises a bypass regulator and means for connecting said bypass regulator to said pump assembly to maintain a constant pressure differential across said pump.

8. A fluid sampler, as defined in claim 3, wherein a third one of said plug-in modules comprises a manually adjustable bypass valve and means for coupling said bypass valve across said pump housing.

9. A fluid sampler, as defined in claim 3, wherein a fourth one of said plug-in modules comprises a vent plug, including means for venting said common case to the atmosphere.

10. A fluid sampler, as defined in claim 9, wherein said vent plug further comprises means for venting said fluid sampler is internal of said common case.

* * * * *